US009717679B1

(12) United States Patent
Cawthon

(10) Patent No.: US 9,717,679 B1
(45) Date of Patent: Aug. 1, 2017

(54) METHODS FOR THE PREVENTION AND TREATMENT OF ANIMAL SKIN CONDITIONS

(71) Applicant: Garret D. Cawthon, Louisville, KY (US)

(72) Inventor: Garret D. Cawthon, Louisville, KY (US)

(73) Assignee: Touchless Designs LLC, Sevierville, TN (US)

( * ) Notice: Subject to any disclaimer, the term of this patent is extended or adjusted under 35 U.S.C. 154(b) by 0 days.

(21) Appl. No.: 14/109,323

(22) Filed: Dec. 17, 2013

Related U.S. Application Data

(60) Provisional application No. 61/797,903, filed on Dec. 17, 2012.

(51) Int. Cl.

| | |
|---|---|
| ***A61K 9/00*** | (2006.01) |
| ***A61K 33/30*** | (2006.01) |
| ***A61K 47/06*** | (2006.01) |
| ***A61K 9/14*** | (2006.01) |
| ***A61K 47/24*** | (2006.01) |
| ***A61K 45/06*** | (2006.01) |
| ***A61K 47/44*** | (2017.01) |

(52) U.S. Cl.
CPC .............. *A61K 9/0017* (2013.01); *A61K 9/14* (2013.01); *A61K 33/30* (2013.01); *A61K 45/06* (2013.01); *A61K 47/06* (2013.01); *A61K 47/24* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 3,079,299 A | | 2/1963 | Heilig |
| 3,584,115 A | | 6/1971 | Gebhart et al. |
| 3,788,521 A | | 1/1974 | Laauwe |
| 3,826,232 A | * | 7/1974 | Duffey et al. ................ 119/652 |
| 3,928,556 A | * | 12/1975 | Sweger ............... A61L 26/0014 424/45 |
| 4,001,391 A | | 1/1977 | Feinstone et al. |
| 4,082,222 A | | 4/1978 | Boris |
| 4,134,523 A | | 1/1979 | Hansen et al. |
| RE30,093 E | | 9/1979 | Burger |
| 4,187,985 A | | 2/1980 | Goth |
| 4,239,407 A | | 12/1980 | Knight |
| 4,307,089 A | | 12/1981 | Mellon et al. |
| 4,382,919 A | | 5/1983 | Alonso et al. |
| 4,389,418 A | | 6/1983 | Burton |
| 4,495,168 A | | 1/1985 | Schmolka |
| 4,510,734 A | | 4/1985 | Banks et al. |
| 4,556,560 A | | 12/1985 | Buckingham |
| 4,816,254 A | | 3/1989 | Moss |
| 4,857,321 A | | 8/1989 | Thomas |
| 4,893,956 A | | 1/1990 | Wojcik |
| 4,937,234 A | | 6/1990 | Fahim |
| 4,963,591 A | | 10/1990 | Fourman et al. |
| 4,981,677 A | | 1/1991 | Thau |
| 4,996,238 A | | 2/1991 | Matravers |
| 4,996,239 A | | 2/1991 | Matravers |
| 5,091,193 A | | 2/1992 | Enjolras et al. |
| 5,110,593 A | | 5/1992 | Benford |
| 5,126,136 A | | 6/1992 | Merat et al. |
| 5,169,037 A | | 12/1992 | Davies et al. |
| 5,176,903 A | | 1/1993 | Goldberg et al. |
| 5,194,261 A | | 3/1993 | Pichierri |
| 5,223,250 A | | 6/1993 | Mitchell et al. |
| 5,229,105 A | | 7/1993 | Wilmsmann |
| 5,249,747 A | | 10/1993 | Hanson et al. |
| 5,256,403 A | | 10/1993 | Gaskin |
| 5,300,286 A | | 4/1994 | Gee |
| 5,330,756 A | | 7/1994 | Steuart et al. |
| 5,362,488 A | | 11/1994 | Sibley et al. |
| 5,366,660 A | | 11/1994 | Tapley |
| 5,409,903 A | | 4/1995 | Polak et al. |
| 5,417,961 A | | 5/1995 | Nearn et al. |
| 5,436,007 A | | 7/1995 | Hartung et al. |
| 5,441,726 A | | 8/1995 | Mitchnick et al. |
| 5,455,033 A | | 10/1995 | Silverman et al. |
| 5,486,631 A | | 1/1996 | Mitchnick et al. |
| 5,527,519 A | | 6/1996 | Miksits et al. |
| 5,531,985 A | | 7/1996 | Mitchell et al. |
| 5,536,492 A | | 7/1996 | Mitchnick et al. |
| 5,536,502 A | | 7/1996 | Mulder |
| 5,582,818 A | | 12/1996 | Nakanishi et al. |
| 5,587,148 A | | 12/1996 | Mitchell et al. |
| 5,609,852 A | | 3/1997 | Galley et al. |
| 5,609,854 A | | 3/1997 | Guerrero et al. |

(Continued)

FOREIGN PATENT DOCUMENTS

| | | | |
|---|---|---|---|
| EP | 191128 | A1 | 8/1986 |
| WO | WO 92/06701 | A1 | 4/1992 |
| WO | WO 99/08649 | A1 | 2/1999 |

*Primary Examiner* — Johann R Richter
*Assistant Examiner* — Katherine Peebles
(74) *Attorney, Agent, or Firm* — Taft Stettinius & Hollister LLP

(57) ABSTRACT

A method for treating a skin condition of an animal includes identifying an animal skin treatment area having a wound, a scratch or other adverse skin condition; optionally making a determination that the treatment area is at risk for skin maceration; and, in response, applying a skin treatment composition to the treatment area. In certain embodiments, the composition comprises a solid particulate material such as zinc oxide, water and a fluid base material selected from the group consisting of mineral oil, silicone oil, plant-based oil and mixtures thereof. The composition may further include additives such as lanolin, petrolatum, and paraffin, among others. In a preferred embodiment, the applying includes spraying the composition on the treatment area, for example by using an atomizer.

25 Claims, 6 Drawing Sheets

(56) References Cited

U.S. PATENT DOCUMENTS

| | | | | | |
|---|---|---|---|---|---|
| 5,618,529 | A | | 4/1997 | Pichierri | |
| 5,639,025 | A | | 6/1997 | Bush | |
| 5,652,274 | A | | 7/1997 | Martin | |
| 5,658,956 | A | | 8/1997 | Martin et al. | |
| 5,674,912 | A | | 10/1997 | Martin | |
| 5,721,306 | A | | 2/1998 | Tsipursky et al. | |
| 5,728,391 | A | | 3/1998 | Ikeya et al. | |
| 5,744,469 | A | | 4/1998 | Tran | |
| 5,762,945 | A | | 6/1998 | Ashley et al. | |
| 5,788,389 | A | | 8/1998 | de Laforcade | |
| 5,869,071 | A | | 2/1999 | Wieselman et al. | |
| 5,874,479 | A | | 2/1999 | Martin | |
| 5,876,688 | A | | 3/1999 | Laundon | |
| 5,879,688 | A | | 3/1999 | Coury et al. | |
| 5,881,925 | A | | 3/1999 | Ando | |
| 5,961,957 | A | | 10/1999 | McAnalley | |
| 6,044,802 | A | * | 4/2000 | Schmid et al. | 119/856 |
| 6,103,245 | A | | 8/2000 | Clark et al. | |
| 6,103,247 | A | | 8/2000 | Boussouira et al. | |
| 6,217,890 | B1 | | 4/2001 | Paul et al. | |
| 6,270,793 | B1 | * | 8/2001 | Van Dyke et al. | 424/443 |
| 6,423,323 | B2 | | 7/2002 | Neubourg | |
| 6,607,716 | B1 | * | 8/2003 | Smith | A61K 8/042 424/642 |
| 6,627,178 | B1 | * | 9/2003 | Cawthon | 424/45 |
| 2008/0206156 | A1 | * | 8/2008 | Cronk | A61K 8/046 424/45 |
| 2008/0317830 | A1 | * | 12/2008 | Goldstein | A61K 33/06 424/447 |
| 2009/0036497 | A1 | * | 2/2009 | Taylor | 514/341 |
| 2011/0077193 | A1 | * | 3/2011 | Gupta | 514/2.7 |

* cited by examiner

METHODS FOR THE PREVENTION AND TREATMENT OF ANIMAL SKIN CONDITIONS

BACKGROUND

A variety of problematic skin conditions afflict animals, these conditions being caused by various etiologies, but typically being manifestations of physical or chemical breakdown of skin. Distressed skin is particularly susceptible to breakdown. Skin conditions may be caused, for example, by injury or other physical trauma, such as for example injury caused by bites, scratches, friction, cuts or other wounds; exposure to the elements, such as for example moisture or extreme temperatures; exposure to chemical irritants; or action of pests, such as, for example, parasites, microbes or insects (e.g., fleas or flies). The conditions can also be caused or exacerbated by infections or by self-inflicted injury (also referred to herein as "self-mutilation"), such as biting or scratching at an irritated area. Self-inflicted injury is a particular concern, as it can aggravate less severe issues, and can increase both healing time and the likelihood of infection, and ultimately could lead to death.

Various topical treatments, such as ointments, creams, and lotions, have been used to treat such animal skin conditions. The most effective of these typically contain pharmaceutical active ingredients. However, issues with proper application limit the effectiveness of the treatment products. For example, many products require a high frequency of application in some cases three to six times per day to maintain adequate treatment. Conventional ointments, creams, and lotions are often applied in thick layers; however, hair or fur can create physical barriers that often reduce the intimate contact of the treatment composition to the skin.

In some instances, topical products formulated for human treatment have been used to treat a skin condition of an animal; however, a common problem with the use of such topical products to treat an animal is the higher incidence of the animal ingesting the product as a result of licking its wound. Ingestion of a pharmaceutically active ingredient that is formulated for human topical use can be very detrimental to the health of the animal. Moreover, products formulated for human use typically also include ancillary ingredients that can enhance the animal's tendency to ingest the product and/or can be detrimental to an animal's health if ingested. Examples of such ancillary ingredients include preservatives, surfactants, and certain fragrances. Application of a thick coating of such ointments and/or matting of the ointment in fur can make poisoning an even greater concern. To combat this issue, skin care products formulated for use on animal are typically highly diluted to reduce their toxicity in the case of ingestion.

Thicker coatings of ointments, creams, and lotions are especially problematic in that they inhibit oxygen from passing through the coating to the skin/wound site. Oxygen is needed to promote cell growth, and starving the wound from oxygen inhibits healing. Moreover, thicker coatings also have the additional problem of inhibiting moisture (e.g., exudate and perspiration) from leaving the skin surface. Containment of such exudate and/or perspiration in contact with the skin can result in skin maceration that weakens the skin, rendering it more susceptible to infection, skin tears, and the like. Moreover, the warm, moist environment promotes microbial and fungal growth that can lead to infection.

Skincare products used for animals are typically less effective than those used on humans for a variety of reasons. Moreover, animals often are not accepting of the product application, which can potentially lead to a dangerous situation for the caregiver. Animals often remove foreign matter from the skin through rubbing or licking, thereby shortening treatment time. Additionally, application of a physical barrier, such as a bandage or dressing, over an ointment to inhibit the animal from contacting or removing the ointment typically further aggravates the animal, resulting in potential further injury incidental to attempts to remove the covering.

There remains a need for improved topical products for treating the skin of an animal that address the one or more of the above and/or other problems and/or improve outcomes compared to products in the prior art. The present invention addresses this need and provides other benefits and advantages.

SUMMARY

While the actual nature of the invention covered herein can only be determined with reference to the claims appended hereto, certain forms of the invention that are characteristic of the embodiments disclosed herein are described briefly as follows.

In general, the present invention is directed to methods of treating and preventing skin conditions common to livestock, household pets, and other animals. The non-toxic compositions described herein applied as described herein lubricate and/or moisturize the skin through a thin layer—for example, less than half a millimeter—of the concentrated formula. A thin coating of one of the disclosed compositions is effective because the water content is considerably below that of other products, providing a hydrophobic formula that strongly and immediately adheres to the skin to create a moisture barrier that is difficult for the animal to remove.

Hydrophobic treatment compositions disclosed herein promote healing of problem skin areas of animals. The compositions have antimicrobial and antifungal properties, are nontoxic, and form a moisture barrier for external moisture while allowing internal moisture (e.g., exudate and perspiration) to diffuse through the coating to prevent maceration. The compositions also allow oxygen to diffuse to the skin through the coating to promote healing. This disclosure also describes the spray application of the compositions to a selected skin treatment area without the need for the person administering the treatment to directly contact the composition or the skin of the animal. Application of the treatment composition is accomplished by forming the composition into a mist or spray using an atomizing spray dispenser.

The compositions and application methods described herein can be used to treat skin conditions found on a wide variety of animals, including livestock (e.g., horse, cow, pig, sheep, and chicken), household pets (e.g., dog, cat, bird, hamster, gerbil, rabbit, guinea pig, ferret, mouse, and even exotic animals such as reptiles and amphibians). The compositions and application methods are also highly effective when used to treat other mammal species (e.g., zoo animals such as elephants, hippos, camels, zebras, etc.) whose skin is susceptible to drying and cracking.

In one form of the invention, a method includes selecting an animal skin treatment area, and applying a treatment composition onto the treatment area. In various embodiments, the selecting includes identifying a skin location having an injury, rash, wound, or other adverse condition. In certain embodiments, the selecting further includes determining a characteristic of the treatment area, for example whether it is sensitive to the touch, or whether it is at risk for skin maceration.

The composition includes a fluid base material, and in certain embodiments further includes a solid particulate material. In some embodiments, the solid particulate material is zinc oxide, and the fluid base material comprises at least one of a mineral oil, a plant-based oil, and a silicone oil. In some embodiments, one or more of the fluid component, the solid component or an additional ingredient has a foul taste, which deters the animal from licking the composition off the skin treatment area, and also deters biting from both the animal and insects.

The composition may further include one or more additives, such as for soothing the wound, providing a selective moisture barrier, fighting infections, modifying the viscosity, or altering the appearance, scent or taste of the composition. These additives can be also selected to be non-toxic for the animal treatments.

Applying the composition is performed such that only the composition comes into contact with the treatment area. In other words, the wound is not contacted by an application medium, such as a swab, pad, or finger. This is accomplished by passing the composition through a spraying mechanism, such as an atomizer or mister.

The compositions and application methods disclosed herein have a variety of advantages over traditional rub-in ointments, creams and lotions in the prior art, including for example one or more of the following: (i) in view of the concentrated, strongly hydrophobic characteristics of various composition embodiments described herein, less material is required for adequate treatment/protection; (ii) spray application substantially reduces the likelihood of skin breakdown that is more likely to occur when using a rub-in ointment; (iii) composition embodiments that are clear/translucent allow viewing of the skin wound bed versus opaqueness associated with traditional ointments; (iv) the composition embodiments are nontoxic to the animals; (v) spray application can be achieved quickly and the applied compositions are resistant to rub-off and run-off; (vi) low viscosity of the compositions under shear provide improved wetting of the skin and have improved ability to by-pass physical barriers such as hair; (vii) spray application reduces waste of the product; (viii) spray application reduces or eliminates physical contact by the caregiver, which can be painful; (ix) skin pain is reduced when treating wounds with open skin and/or exposed nerve endings by the oily ingredients coating and "sealing" the wound site; (x) oxygen is allowed to transfer to the skin/wound site at a higher rate; (xi) moisture (e.g., exudates and perspiration) is allowed to transfer from the skin/wound site at a higher rate to prevent maceration of the skin; (xii) drying is avoided in embodiments with high oil content and low water content; (xiii) use of non-flavorful ingredients and/or foul-tasting additives deter an animal from self-mutilation and also can repel or inhibit insects; (xiv) highly hygroscopic composition embodiments adhere to the skin and are difficult to rub-off or wash-off; (xv) highly hygroscopic composition embodiments dehydrate and kill bacteria and fungi on the skin; and (xvi) highly hydrophobic composition embodiments protect the skin from external moisture.

Further embodiments, forms, features, aspects, benefits, objects, and advantages of the present invention will become apparent from the detailed description and figures provided herewith.

DETAILED DESCRIPTION

Figure 1:
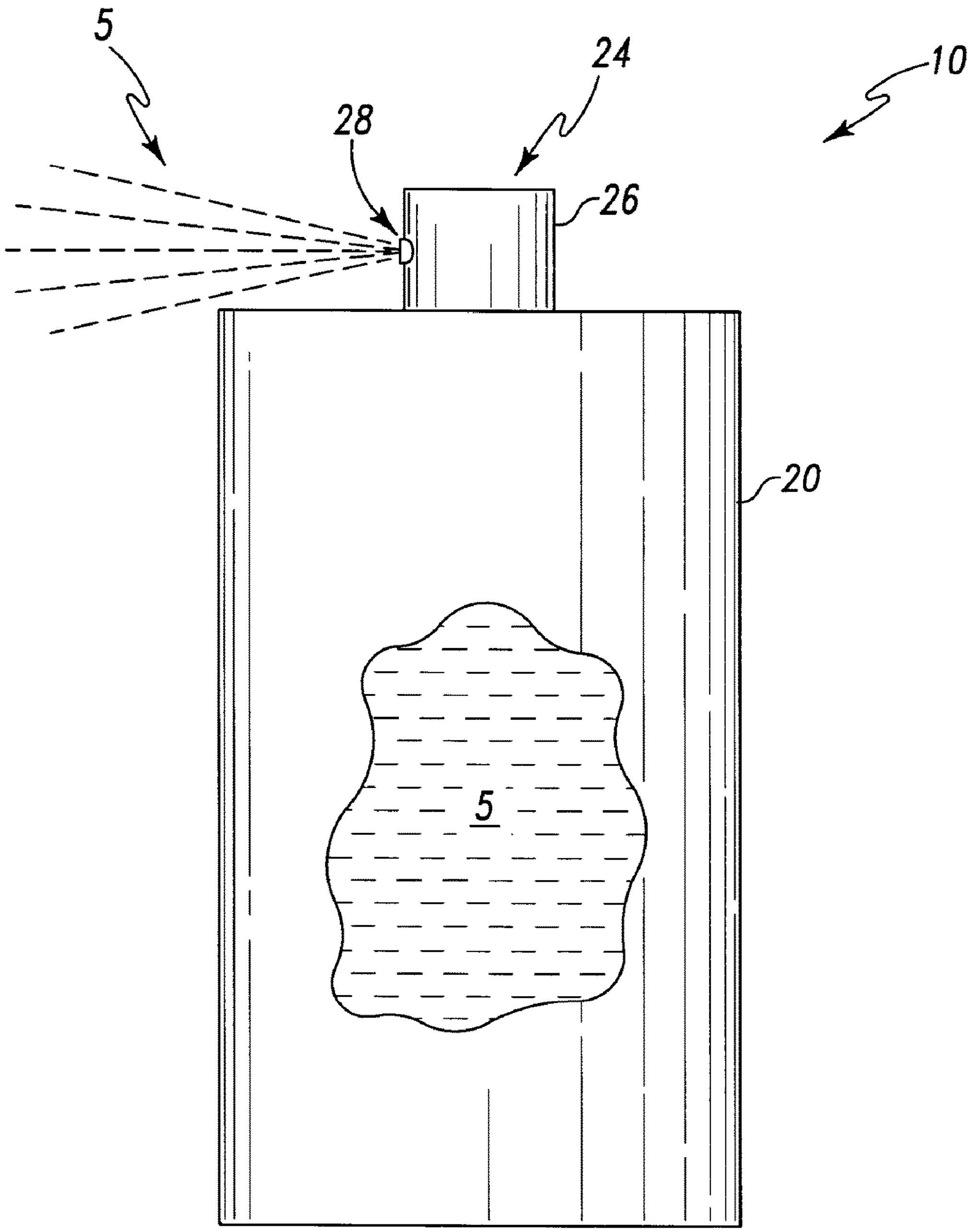
FIG. 1 is a side elevational view, with a cut-out portion, of an exemplary atomizing spray dispenser.

For the purposes of clearly, concisely and exactly describing exemplary embodiments of the invention, the manner and process of making and using the same, and to enable the practice, making and use of the same, reference will now be made to certain exemplary embodiments, including those illustrated in the figures, and specific language will be used to describe the same. It shall be understood that no limitation of the scope of the invention is thereby created, and that the invention includes and protects such alterations, modifications, and further applications of the exemplary embodiments as would occur to one skilled in the art to which the invention relates.

The present disclosure involves treatment compositions and methods that promote healing to common skin problems that afflict a variety of animals. The nontoxic compositions described herein are both antimicrobial and antifungal because they are hygroscopic, removing critical water necessary for microorganisms to live and grow. In addition, the compositions form a hydrophobic moisture barrier to protect the skin from external moisture (e.g., urine, feces, rain water) while allowing internal moisture (e.g., exudate and perspiration) to diffuse through the coating to prevent maceration. Moreover, oxygen can transfer back through the coating to the skin to promote cell growth and healing. Due to the high level of hydrophobic fluids (e.g., mineral oil, silicone oil, plant-based oil, or mixtures thereof), the compositions do not become dried and caked on the skin over extended periods of time, minimizing friction and irritation while lubricating the skin over extended periods of time.

The compositions and methods disclosed herein address a number of problems associated with treating animal wounds and other adverse skin conditions by providing methods, compositions and systems for treatment involving application of a composition as an atomized spray. This eliminates the often painful rub-in application required by conventional ointments, which can result in physical resistance from the animal. A spray also reduces physical contact between animal and caregiver, which can reduce infection risk for both. The term "animal" as used herein is defined as a non-human animal. Similarly, the term "mammal" as used herein is defined as a non-human mammal. In one embodiment the animal is a livestock animal, such as, for example, a horse, cow, pig, goat, sheep or chicken. In another embodiment the animal is a household pet, such as, for example, a dog, cat, bird, hamster, gerbil, rabbit, guinea pig, ferret or mouse. In yet other embodiments, the animal is a reptile or an amphibian. These lists are not intended to be limiting, however, it being understood that the present disclosure contemplates treatment of additional animals as well, such as, for example, an animal housed at a zoo.

Provided by the present disclosure are methods for applying a variety of treatment compositions to a selected animal skin treatment area without the need for the person administering the treatment to directly contact the composition or the skin of the animal. Generally speaking, the method includes selecting an animal skin treatment area having an injury, wound, or other adverse skin condition, and in response to the selecting, applying a treatment composition onto the treatment area. Illustrative embodiments of the composition and the delivery mechanism will be first described, followed by processes for selecting the treatment area.

Referring to FIG. 1, to practice the method, a treatment composition 5 is placed into an atomizing spray dispenser 10. The dispenser is preferably a container 20 equipped with a spray delivery mechanism 24 configured to atomize and propel the composition toward a treatment surface. Compositions described herein exhibit excellent features for the treatment of animal skin conditions. When a proper amount of the composition is atomized and propelled by a suitable atomizing spray delivery mechanism, the composition forms a coating over the skin surface, thereby providing a barrier to moisture, and a soothing function to the skin.

It is preferred that the composition have a suitably low viscosity that it may be readily converted to an atomized spray, but that the viscosity not be too low because a viscosity that is too low may result in the composition running off of the treatment surface. The composition may comprise a liquid, a combination of liquids or a combination of one or more liquids and one or more solids that features a suitable viscosity. The proper viscosity can be attained at least in part by the selection of a fluid base material.

The term "fluid base material" is used herein to refer to a fluid into which additional ingredients may be mixed, dissolved and/or suspended. In one embodiment the fluid base material comprises an oil having a viscosity of from about 1 centipoise to about 1000 centipoise. Exemplary oils that may be used are mineral oils, silicone oils, plant-based oils or mixtures thereof. The term "mineral oil" is used herein to refer to a liquid petroleum derivative. Exemplary commercially available mineral oils that may be used include Witco Corporation's CARNATION™ Mineral Oil (having a viscosity range of 9-12 centipoise) or Penreco Corporation's DRAKEOL™ 7 Mineral Oil (having a viscosity of 9-11 centipoise).

The term "silicone oil" is used herein to refer to a liquid silicone composition. Exemplary silicone oils that may be used, for example, are cyclomethicone, dimethicone and derivatives thereof. Commercially available silicone oils include Dow Corning Corporation's 200 polydimethylsiloxane fluids and GE Silicones' SF series of low viscosity dimethyl fluids. Cyclomethicone is a volatile compound, and is advantageously included in certain inventive compositions because it evaporates when applied to the skin's surface, making the coating more dry to the touch. Other volatile compounds may also be used in this way, including, for example, an organic solvent such as isododecane. Such compounds are particularly useful in embodiments that utilize an aerosol dispenser as the delivery mechanism (described in more detail below), because the volatile compounds may be used as liquid solvents in the container that evaporate when dispensed from the container, leaving a drier coating on the skin surface.

The term "plant-based oil" is used herein to refer to a non-petroleum biomass derived oil, such as a vegetable or fruit oil. By way of non-limiting example, the plant-based oil may include, for example, at least one of linseed oil, jojoba oil, rapeseed oil, soybean oil, grape seed oil, and sunflower oil. It is of course not intended that the fluid base material be limited to the above exemplary compositions. As an alternative to plant-based oil, silicone oil and mineral oil, another material that may be used as the fluid base material, or included therein, is cod liver oil.

The fluid base material may alternatively be water, an oil-in-water emulsion or a water-in-oil emulsion. Inventive compositions including water or an emulsion as the base material may be preferable for some uses, as such compositions have a less greasy feel. The inclusion of water in the composition can provide additional advantages, such as reducing the cost of the composition, providing a source of moisture for dry skin, and enabling inclusion of additional hydrophilic ingredients that would not become suitably dissolved or dispersed in an oil-based composition.

When water is included in a composition that also comprises one or more oils, it is readily understood that an emulsifying agent will typically be necessary to produce a stable mix of the water and nonaqueous ingredients in the composition. Examples of suitable emulsifiers that may be used include cetyl alcohol, stearyl alcohol, cetearyl alcohol and glycerol monolaurate. It is of course not intended that this list be limiting but simply provide examples of emulsifiers that may be used. Additional suitable emulsifiers are set forth on pages 90 to 94 of the C.T.F.A. Cosmetic Ingredient Handbook, First Edition, 1988, which is hereby incorporated by reference. Further guidance to the preparation of stable emulsions generally may be found in U.S. Pat. No. 5,417,961 to Nearn et al., which is hereby incorporated by reference in its entirety.

In certain embodiments, the composition comprises at least about 1 percent solid particulate material by weight and at least about 20 percent by weight of a fluid base material. The solid particulate material may include one or more of particulate zinc oxide, talc, calamine or kaolin. Each of these particulate materials is hygroscopic—that is, they tend to absorb water. The hydrophobic oil-based fluid restricts the diffusion of water to the hygroscopic solid, resulting in a controlled absorption of moisture, so as to not over-dry the skin's surface.

The hygroscopic components help absorb moisture—such as exudate and perspiration—that diffuses through the skin surface. Other absorptive compounds, for example, humectants, could be used for this purpose, but the preferred materials (zinc oxide and petrolatum, discussed below) are also FDA-approved active ingredients as skin protectants. Thus, the preferred compositions can have the recommended concentrations of skin protectants while minimizing additional ingredients that could be irritating, or have other side-effects.

The low water fraction in the hydrophobic formulas reduces the amount of caking on the skin as the water evaporates. This is in contrast to the hard, gritty residue resulting from the drying of ointments, lotions, and creams. Such residue irritates the skin, and creates additional friction for skin-to-skin and other contact areas. The compositions used in the inventive methods claimed herein may retain liquidity on the skin. The liquidity of the composition enables it to continue lubricating the skin, thereby minimizing friction and shear, and may also enable the composition to continue to knead the therapeutic ingredients into the skin's cracks and crevices.

One advantage of this formulation is that moisture, either as perspiration or exudate, can readily leave the skin through the coating; the skin remains dry because the moisture cannot re-adhere to the skin due to the highly hydrophobic nature of the coating. The body's internal pressure that forces the liquid through the skin is sufficient to overcome the barriers associated with the hydrophobicity and diffusional resistance associated with the coating. This is in contrast to the thicker coating associated with ointments that trap and accumulate moisture intimately on the skin surface, leaving the skin vulnerable to maceration.

In embodiments in which the particulate material include zinc oxide, the zinc oxide can have an average particle size of from about 0.01 microns to about 100 microns. In another embodiment the average particle size is from about 0.01 microns to about 10 microns and in yet another embodiment from about 0.01 microns to about 1 micron. Zinc oxide particles of from about 0.01 microns to about 0.1 microns are commonly referred to as microfine zinc oxide particles. A feature of microfine zinc oxide that is desirable in some applications is that the microfine zinc oxide is translucent when dispersed in a conventional fluid base material. Compositions including microfine zinc oxide therefore do not have the characteristic opaque white appearance of formulations including zinc oxide of larger particle sizes. It is also believed that microfine zinc oxide provides additional advantages over larger particulates, including a smoother film coating on the skin, lower viscosity at the same overall zinc oxide loading, better penetration of the zinc oxide into the skin's cracks and crevices, more even coverage, and higher surface area providing for more reaction and therapeutic activity.

It is also intended that the term "zinc oxide" encompass coated zinc oxides. A typical coating is silicone-based and is used to help disperse the zinc oxide in solution and to lower the viscosity of a zinc oxide mixture. It has been reported that uncoated zinc oxide particles swell in certain solvents, such as, for example, octyl palmitate. One advantage of using coated zinc oxide is that silicone coated zinc oxide particles are hydrophobic, non-reactive and not affected by water. Coated hydrophobized zinc oxides or particles also have a significantly decreased photoreactivity, which makes them more resistant to degradation and more chemically inert than non-coated zinc oxides. Hydrophobized zinc oxide is therefore particularly useful in compositions that are applied to skin that is exposed to sunlight or other ultraviolet radiation.

The ratio of zinc oxide to fluid base material in this composition is preferably selected such that the composition has a predetermined viscosity at a given temperature. It is readily understood that the ratio selected is dependent upon the desired viscosity for a given system. For example, different delivery systems may function optimally when used to deliver compositions having different overall viscosities. Further, the preferred ratio also depends upon the viscosity of the fluid base material selected for use and upon the particle size distribution of the zinc oxide. These and other factors may be readily determined and considered by a person of ordinary skill in the art, without undue experimentation, to make an inventive composition having a suitable viscosity. The composition in one embodiment comprises from about 1 to about 40 percent zinc oxide by weight. In alternative embodiments, the zinc oxide content of the composition is from about 5 to about 25 percent or from about 10 to about 15 percent. In one embodiment, the composition comprises from about 20 to about 99 percent fluid base material by weight. In alternative embodiments, the fluid base material content of the composition is from about 33 to about 80 percent or from about 55 to about 75 percent.

The composition may also optionally include one or more of a wide variety of beneficial additives that may be incorporated for a variety of reasons. For example, the composition may comprise a skin conditioning agent, for example lanolin or various vitamin agreements. It is understood that the term "lanolin" refers to the various forms of lanolin and its derivatives, such as, for example, lanolin oil, lanolin wax, and lanolin alcohols.

The composition may also include a moisture barrier material, such as paraffin, microcrystalline wax. Additionally or in the alternative, the moisture barrier material may include a hygroscopic petrolatum. Additional ingredients that may optionally be included in a composition are fragrances, dyes, preservatives, anti-bacterial agents, anti-fungal agents and emollients. It is of course not intended that this list limit the scope of the invention, but simply provide examples of ingredients that might be included in the compositions.

When including one or more beneficial additives, it is important to consider the effect that the one or more additives have on the overall viscosity of the composition. Thus, adjustments of the zinc oxide to fluid base material ratio may be necessary to achieve a proper viscosity when including one or more additives to achieve a desired combination of additional features.

In certain exemplary embodiments, the composition may also include from about 1 to about 16 percent lanolin by weight. In other alternative embodiments, the lanolin content of the composition is from about 5 to about 15 percent or from about 5 to about 10 percent. The composition may further include from about 1 to about 25 percent petrolatum by weight. In other alternative embodiments, the petrolatum content of the composition is from about 5 to about 15 percent or from about 5 to about 10 percent.

An exemplary composition in the practice of the invention comprises from about 1 to about 40 percent zinc oxide, from about 20 to about 99 percent fluid base material, from about 0 to about 16 percent lanolin and from about 0 to about 25 percent petrolatum, all by weight. In one embodiment, the fluid base material comprises from about 20 to about 100 percent mineral oil and from about 0 to about 20 percent silicone oil by weight. Alternatively, the fluid base material may comprise from about 20 to about 100 percent silicone oil and from about 0 to about 20 percent mineral oil by weight.

Another composition embodiment comprises from about 5 to about 25 percent zinc oxide, from about 33 to about 80 percent fluid base material, from about 5 to about 15 percent lanolin and from about 5 to about 15 percent petrolatum, all by weight. An additional composition embodiment comprises from about 10 to about 15 percent zinc oxide, from about 55 to about 75 percent fluid base material, from about 5 to about 10 percent lanolin and from about 5 to about 10 percent petrolatum, all by weight. The composition may also advantageously include from about 5 to about 10 percent talc and/or microcrystalline wax to increase the viscosity of the composition. In one embodiment, the composition is clear or translucent.

A composition that has been found to have particularly excellent features in accordance with the invention comprises about 25 percent zinc oxide, about 5 percent lanolin, about 5 percent petrolatum, about 5 percent microcrystalline wax, about 40 percent mineral oil and about 20 percent cyclomethicone, all by weight.

As mentioned above, other additives may be included in various alternative composition embodiments, including conventional additives typically employed in skin care compositions. For example, fragrance oils may be used to mask the odor of other ingredients and/or for cosmetic appeal. Dyes may also be used to color the composition. In addition, preservatives, such as, for example, DMDM hydantoin, methylparaben or other esters of parahydroxy benzoic acid, and the ester of propylparahydroxy benzoic acid and benzethonium chloride may be used. Other emollients such as aloe vera and vitamins A, D and E may also be used. Emulsion compositions described herein can also optionally include additional active ingredients such as antimicrobial agents, antibacterial agents and antifungal agents.

In one embodiment, the composition has a viscosity of from about 1 to about 1000 centipoise, measured at room temperature using a Brookfield viscometer. In another embodiment, the viscosity is from about 200 to about 700 centipoise. In yet another embodiment, the viscosity is from about 300 to about 500 centipoise.

In one embodiment, the composition comprises 1 percent to 40 percent by weight of a solid particulate material such as zinc oxide, 20 percent to 99 percent by weight of a fluid base material such as mineral oil, silicone oil, plant-based oil and mixtures thereof, and up to 30% by weight of water. In these and other embodiments, the composition may further comprise one or more member selected from the group consisting of talc, lanolin, cod liver oil, petrolatum, paraffin wax and microcrystalline wax. In these and other embodiments, the composition may include at least one of a fragrance, a dye, a preservative, and an emollient.

In another illustrative embodiment, the composition comprises 20 percent to 30 percent by weight zinc oxide, 30 percent to 60 percent by weight of a fluid base material comprising mineral oil and cyclomethicone, 1 percent to 16 percent by weight of lanolin, 1 percent to 25 percent by weight of petrolatum and 1 percent to 10 percent by weight of microcrystalline wax.

In certain embodiments, the composition comprises 5 percent to 30 percent zinc oxide by weight; and 20 percent to 95 percent by weight of a fluid base material comprising at least one of mineral oil, silicone oil, and plant-based oil.

In an exemplary embodiment, the composition comprises 10 percent to 15 percent zinc oxide by weight, 1 percent to 16 percent by weight lanolin, 1 percent to 25 percent by weight petrolatum, up to 30 percent by weight water, and 47 percent to 97 percent by weight of a fluid base material comprising at least one of mineral oil, silicone oil, and plant-based oil.

In another exemplary embodiment, the composition comprises 10 percent to 30 percent by weight of hydrophobized zinc oxide, and 20 percent to 90 percent by weight of a fluid base material selected from the group consisting of mineral oil, silicone oil, plant-based oil and mixtures thereof.

In certain embodiments, the composition comprises particulate zinc oxide, at least one of an anti-bacterial and an anti-fungal material, and at least one of a mineral oil, a silicone oil, a plant-based oil, and cod liver oil.

A composition as described above may be made by mixing the ingredients and heating the mixture to an elevated temperature below the decomposition temperature of the ingredients. Heating is useful to ensure that any solid ingredients are melted, dissolved and/or dispersed in the composition and to more efficiently and stably achieve an acceptable degree of mixing. The mixture is preferably heated to a temperature in a range of from about 40° C. to about 75° C. When temperature sensitive ingredients, such as, for example, vitamin additives or fragrances, are included in an inventive composition, these ingredients should be added after the mixture's temperature has been lowered to below about 40° C. A high shear mixer, such as a triple roll mixer or Charles Ross & Son Company's high-speed mixer-emulsifier, may advantageously be used to assist in the development of a uniform, stable composition.

Referring to FIG. 1, the composition can be applied to a skin treatment surface by atomizing the composition 5 and propelling the atomized composition toward the surface using a suitable atomizing spray dispenser 10 comprising a container 20 and an atomizing spray delivery mechanism 24. The illustrated atomizing spray delivery mechanism 24 releases the composition 5 from the container 20 through an outlet port 28 when a valve is mechanically actuated. In the illustrated embodiment, the mechanism 24 features a reciprocating actuator 26.

Figure 2:
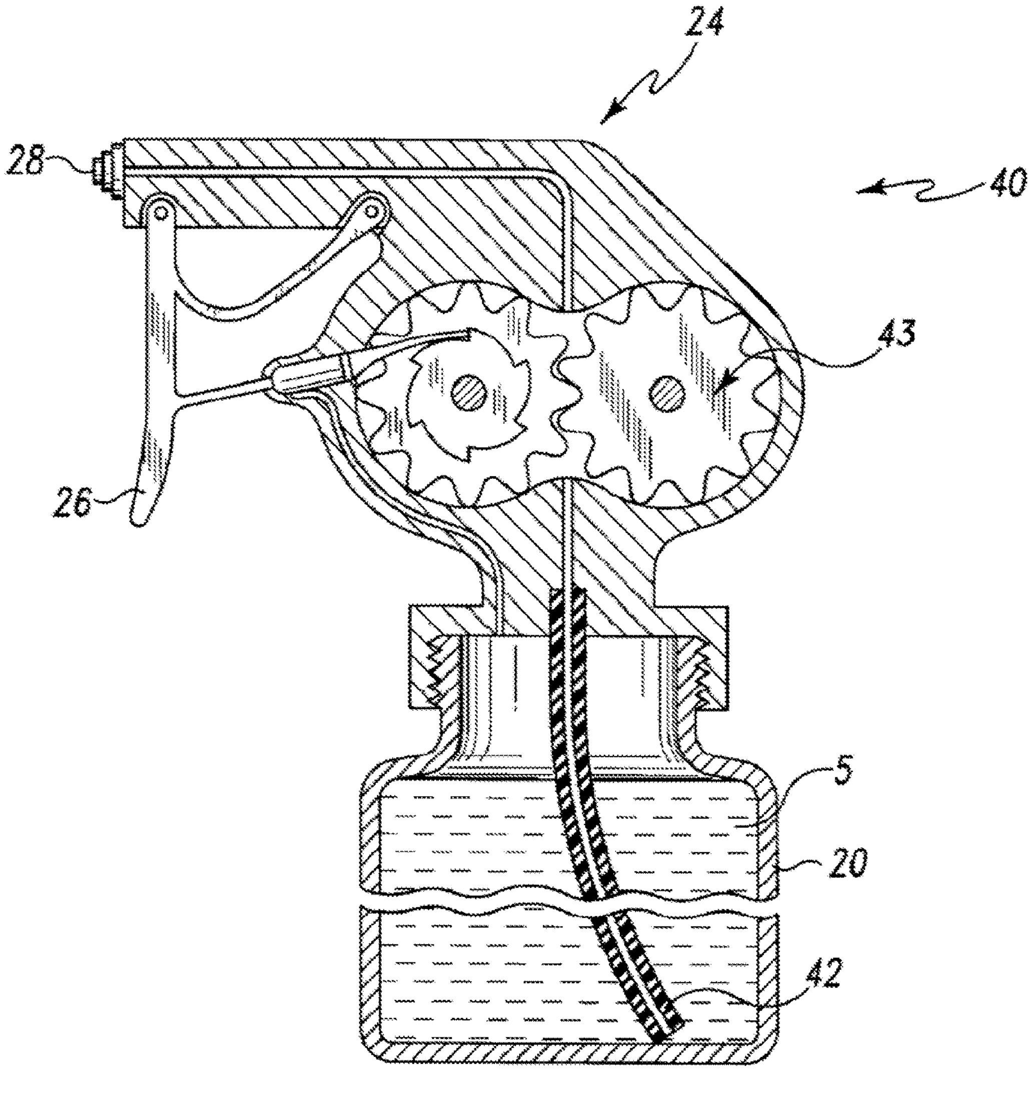
FIG. 2 is a sectional side elevational view of a representative atomizing pump spray dispenser.

An exemplary atomizing spray delivery mechanism that may be used in accordance with the invention is an atomizing pump spray dispenser 40, a representative example of which is depicted in FIG. 2. As used herein, the term "atomizing pump spray dispenser" is intended to refer to a device that, upon activation of a mechanical pump, such as gear pump 43 of FIG. 2, draws a composition 5 from a container 20, atomizes the composition, and propels the atomized composition substantially in a predetermined direction. It is understood that the composition 5 drawn from container 20 preferably enters a conduit in fluid communication with the pump and having an inlet port 42 positioned near the bottom of container 20. "Atomizing" a composition refers to the separation of the composition into relatively small unitary masses (i.e., typically on the order of about 1 to about 100 microns).

It is important to recognize that the term "pump dispenser" has been used in the prior art to refer to devices for drawing a cream, lotion or ointment from a container and propelling a stream of the cream, lotion or ointment, such as, into the palm of ones hand. This type of dispenser is distinguished from an "atomizing pump spray dispenser" as described herein, because a pump dispenser for propelling a stream of a cream, lotion or ointment is incapable of atomizing the cream, lotion or ointment into an atomized mist or spray. It is understood that the unitary masses, when propelled from an atomizing pump spray dispenser, form a mist or a spray. When the atomized composition is directed toward a given surface at a suitable velocity, the unitary masses adhere to the surface to provide a thin, often buttery, coating of the composition on the surface.

A wide variety of atomizing pump spray dispensers are commercially available, as are a wide variety of designs for actuating the dispensers and for atomizing the composition. While it is not intended that the invention be limited by the design of the atomizing pump spray dispensers, representative examples are set forth in U.S. Pat. No. 5,639,025 to Bush, U.S. Pat. No. 5,881,925 to Ando, and U.S. Pat. No. 5,249,747 to Hanson et al.

Another atomizing spray dispenser that may be used in accordance with the invention is a pressure release device. As used herein, the term "pressure release device" is intended to refer to a device that contains a composition under pressure, and, when actuated, opens a valve to release the composition from the pressurized compartment, atomizes the composition, and propels the atomized composition substantially in a predetermined direction by using energy provided by the force of the pressure. The composition may advantageously be maintained under pressure by placing the composition in a pressurized compartment of the container. The composition is releasably contained in the pressurized compartment and when a manually actuating valve is opened, the composition is released from the compartment, atomized, and released from the device as an atomized spray.

Figure 3:
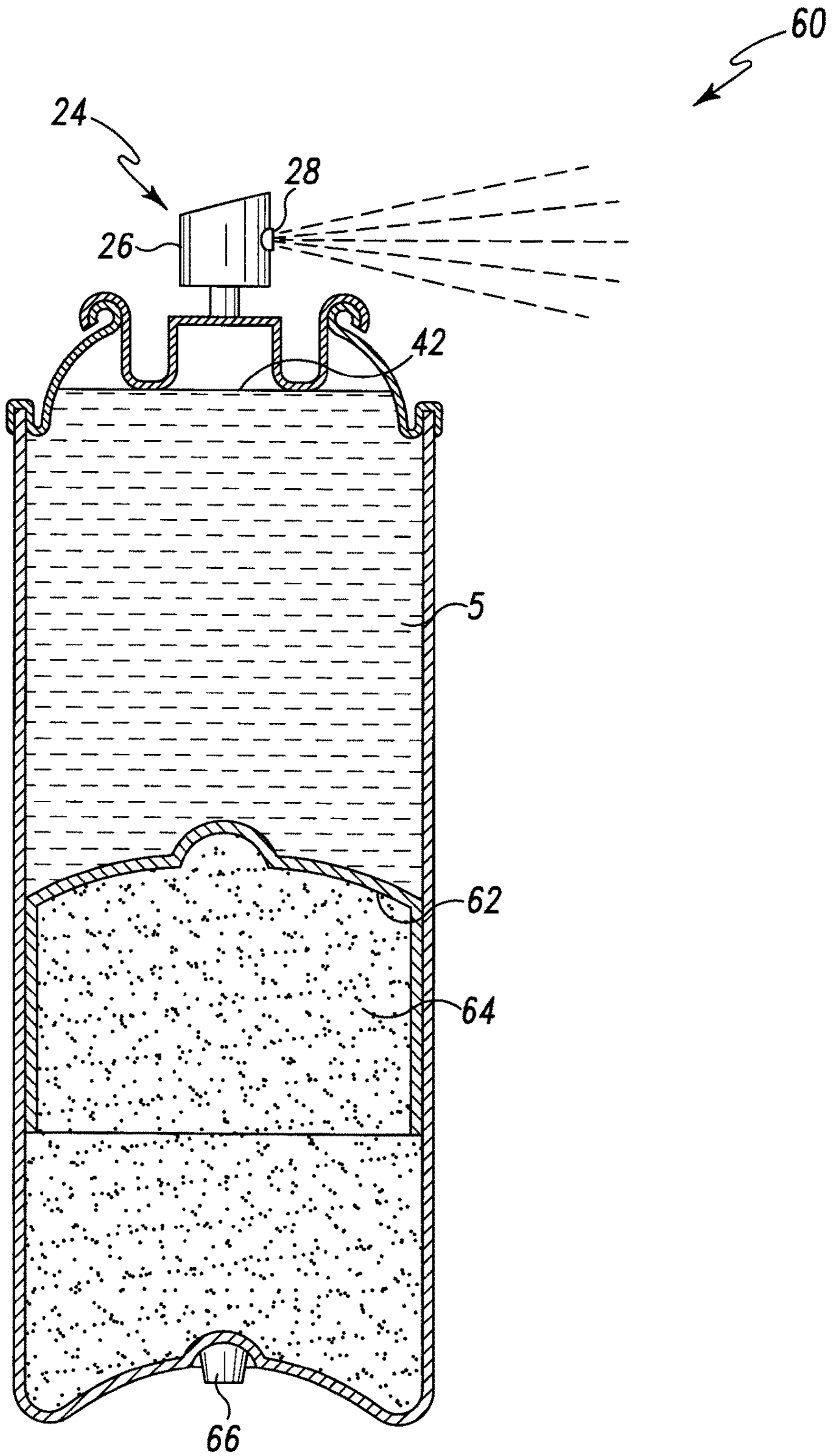
FIG. 3 is a sectional side elevational view of a representative piston-style dispenser.

In certain embodiments, a representative example of which is depicted in FIG. 3, the pressure release device is a piston-style dispenser 60, and pressure is maintained on the composition 5 by pressure of a piston 62. In the illustrated embodiment, the pressure of the piston 62 is provided by placement of a pressurized gas 64 beneath the piston 62, which placement may be advantageously achieved by introducing gas 64 through a gas charging port 66. Alternatively, pressure on the piston may be achieved by a spring loaded mechanism beneath the piston. Such piston-style dispensers are commercially available, as are a wide variety of designs for actuating the dispensers and for atomizing the composition contained therein. While it is not intended that the invention be limited by the design of the piston-style can, representative examples are set forth in U.S. Pat. No. 4,134,523 to Hansen.

Figure 4:
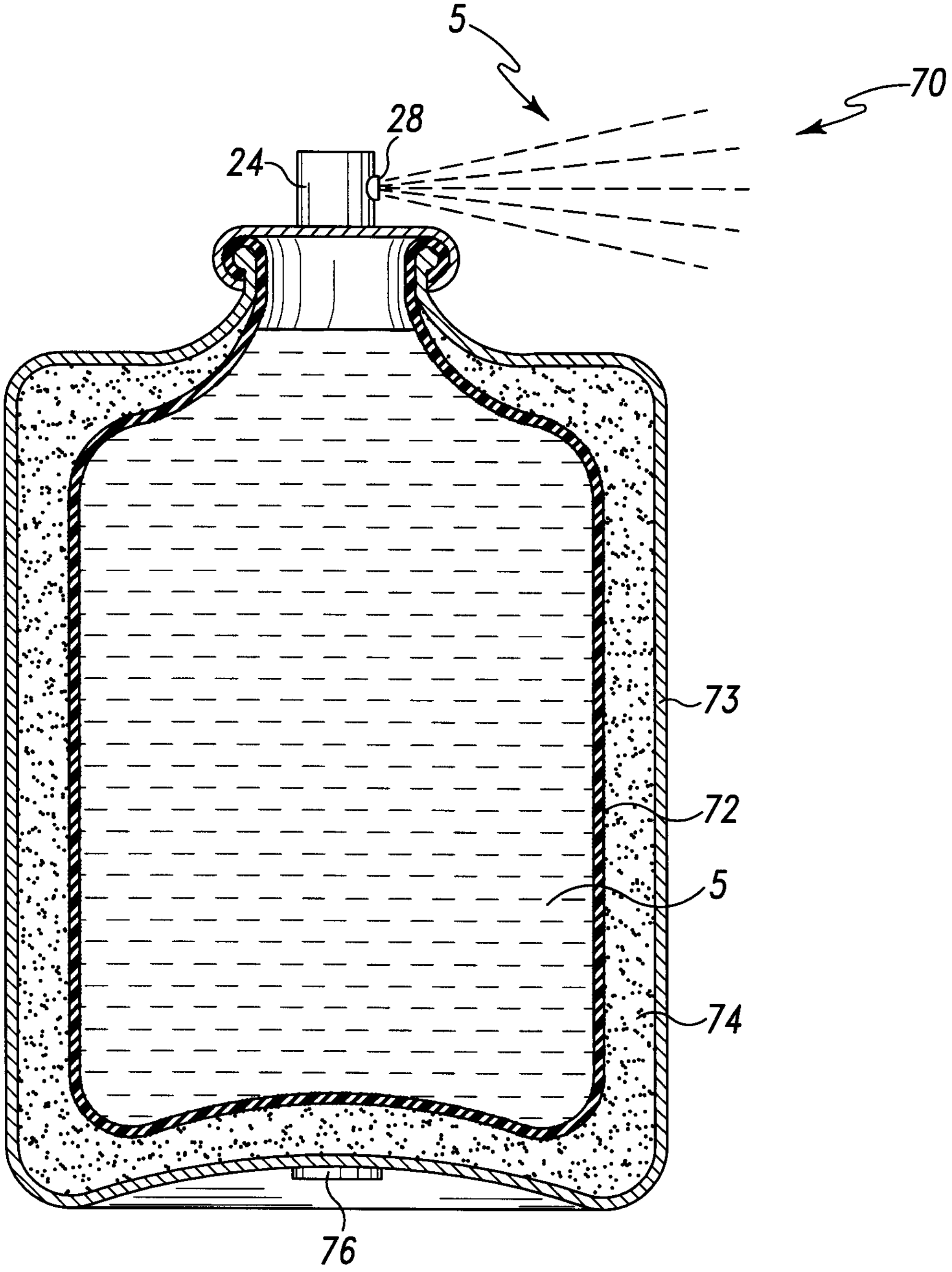
FIG. 4 is a sectional side elevational view of a first representative bag-in-can style dispenser.
Figure 5:
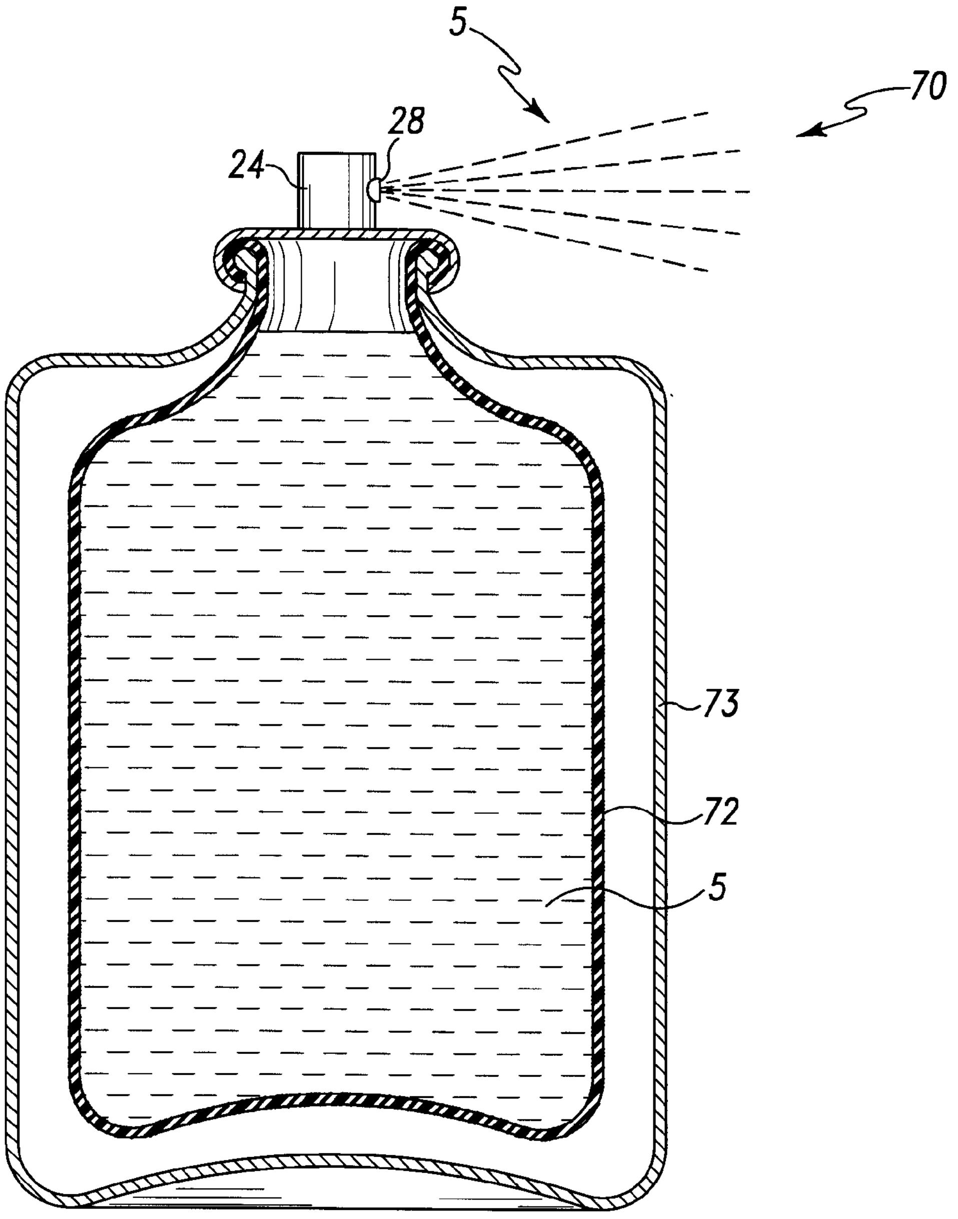
FIG. 5 is a sectional side elevational view of a second representative bag-in-can style dispenser.

In other embodiments, representative examples of which are depicted in FIGS. 4 and 5, the pressure release device comprises a bag-in-can-style dispenser 70. The pressurized compartment of such a container is a polymeric bag 72 received inside a rigid can 73. Pressure is maintained on the composition 5 inside the bag 72. In one embodiment, a representative example of which is depicted in FIG. 4, the pressure is maintained upon the composition by a pressurizing gas 74 received in the can 73 and externally to the bag 72. In the illustrated embodiment, the pressurizing gas 74 can be placed in the can 73 by introducing gas 74 through a gas charging port 76. In another embodiment, an example of which is depicted in FIG. 5, the bag 72 is an elastic shape-memory bag, and pressure is maintained upon the composition 5 by maintaining the bag in an expanded state. This type of container is commonly referred to as a bladder pack container.

A wide variety of bag-in-can-style containers are commercially available, as are a wide variety of designs for actuating the dispensers and for atomizing the composition contained therein. While it is not intended that the invention be limited by the design of the bag-in-can-style container, representative examples are set forth in U.S. Pat. No. 3,788,521 to Laauwe, U.S. Pat. No. 4,510,734 to Banks et al., and U.S. Pat. No. 5,249,747 to Hanson et al.

Figure 6:
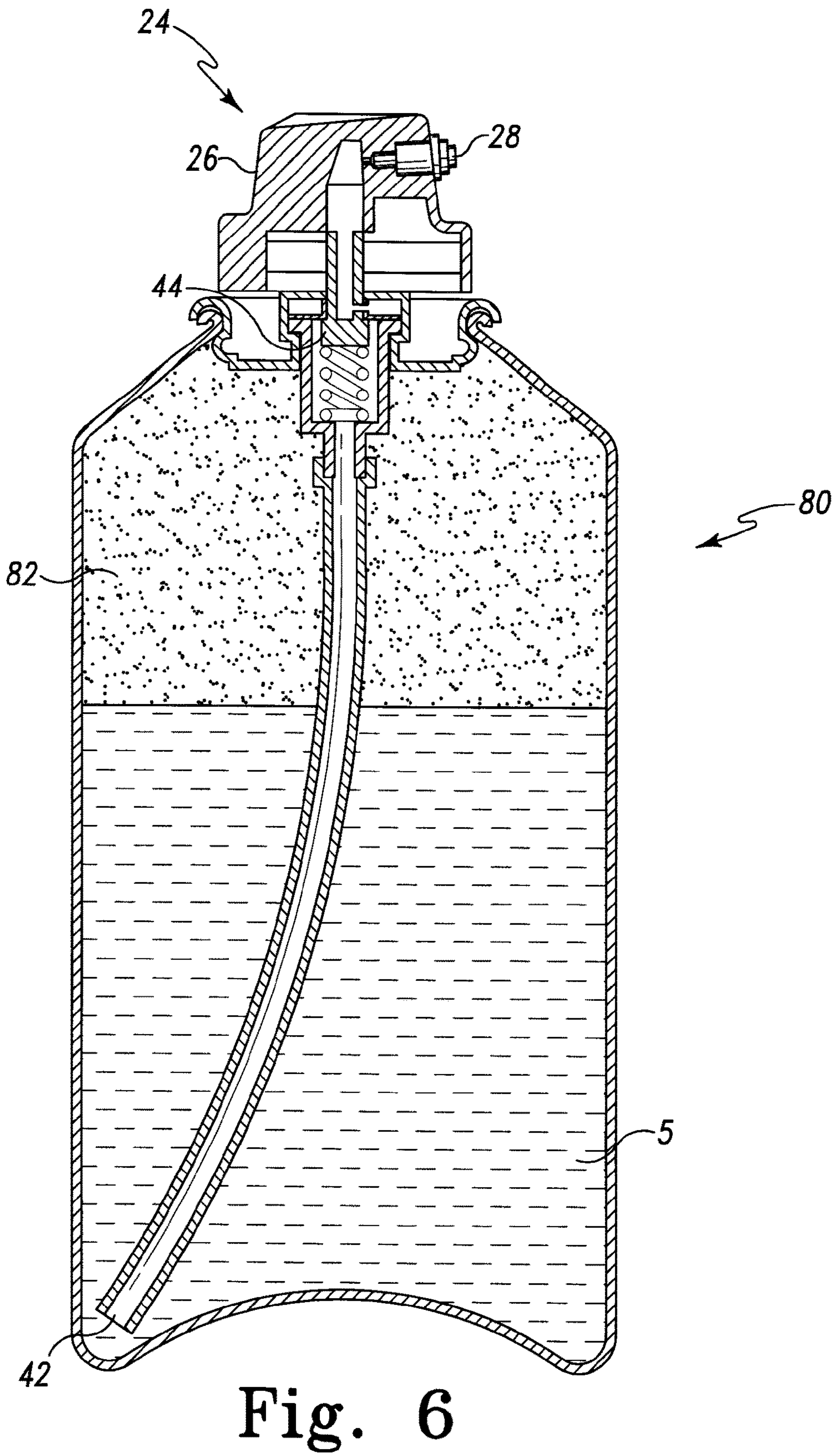
FIG. 6 is a sectional side elevational view of a representative aerosol dispenser.

Another atomizing spray dispenser that may be used in accordance with the invention, a representative example of which is shown in FIG. 6, is an aerosol device 80. As used herein, the term "aerosol device" is intended to refer to a device that delivers the spray treatment composition by entraining the same in a carrier stream comprising an inert pressurized propellant gas 82. When such a device is actuated, the composition is released from the container, entrained in a gaseous stream, atomized, and propelled substantially in a predetermined direction by using energy provided by the pressurized gas. It is understood that the composition and carrier gas may alternately be contained in the container in a pre-mixed form, whereby actuation of the device results in a substantially constant release of the mixture. A wide variety of aerosol containers are commercially available, as are a wide variety of designs for actuating the dispensers and for atomizing the compositions contained therein. While it is not intended that the invention be limited by the design of the aerosol container, representative examples are set forth in U.S. Pat. No. 4,001,391 to Feinstone et al., U.S. Pat. No. 4,187,985 to Goth, U.S. Pat. No. 4,239,407 to Knight, U.S. Pat. No. 4,495,168 to Schmolka, U.S. Pat. No. 5,788,389 to de Laforcade, and U.S. Pat. No. RE030,093 to Burger.

While a wide variety of configurations and styles of atomizing spray dispensers are known in the art, the known prior art does not disclose or suggest the present invention, in which excellent treatment compositions are delivered to an animal skin surface from an atomizing spray dispenser. In view of the above, one system that may be used to achieve efficient treatment is depicted in FIG. 1 and includes a treatment composition as described herein and an atomizing spray dispenser 10 for atomizing the composition and delivering the atomized composition to an animal skin treatment area. In the illustrated embodiment, the dispenser 10 comprises a container 20, an atomizing spray delivery mechanism 24 affixed to the container 20, and the composition 5 positioned in the container 20. The mechanism includes an inlet port in fluid communication with the interior of the container for receiving the composition, a device for atomizing the composition, and an outlet port for propelling the atomized composition substantially in a predetermined direction. It is readily understood that, in use, the inlet port must be in contact with the composition. In other embodiments, the spraying or atomizing may be achieved through the use of an atomizing pump spray dispenser, a piston-style dispenser, or an aerosol dispenser, as described above.

Having illustrated and described the composition and the delivery mechanism, exemplary methods for selecting an animal skin treatment area will now be described.

In certain embodiments, the selecting includes identifying an animal skin treatment area having a wound. In certain embodiments, the selecting includes identifying an animal skin treatment area having a weeping wound. In other embodiments, the selecting includes identifying an animal skin treatment area having a pressure ulcer. In some embodiments, the selecting includes identifying an open wound on the skin of the animal.

The selecting may further include determining a condition of the treatment area. For example, the selecting may include determining that the skin treatment area is at risk for maceration, and applying the composition based at least in part upon the determining. Alternatively, the selecting may include determining that the treatment area is at risk for dryness or cracking.

The selecting may include determining that the treatment area will be exposed to ultraviolet radiation, for example due to exposure to the sun. In response to the determining, the composition applied to the treatment area may comprise a particulate matter including hydrophobized zinc oxide, for example to prevent degradation of the composition or radiation damage to the underlying wound.

In certain embodiments, the selecting includes determining that the wound would benefit from both oxygen diffusion and a selective barrier to the passage of liquid. This may be based at least in part upon the nature of the wound. For example, open wounds and weeping wounds may require more oxygen diffusion than minor cuts and abrasions. In response to the determining, the composition is applied to the wound.

In some embodiments, the selecting includes determining that the skin treatment area is sensitive to the touch, for example due to exposed nerve endings. In such a case, physical contact with the treatment area—as would occur with a conventional ointment—may result in an adverse reaction from the animal, such as kicking, biting, or scratching. The selecting may therefore further include determining that physical contact with the treatment area is likely to irritate the animal, which may result in one or more of the above-listed adverse reactions. In response to the determining, the composition is sprayed onto the treatment area such that the treatment area does not come into contact with an applicator, thereby reducing the discomfort to the animal.

The selecting may include identifying a skin treatment area having both an open wound and either hair or fur growing in or around the wound. In such a case, the composition is sprayed onto the treatment area. The relatively low viscosity of the composition allows it to bypass the hair, such that more complete coverage of the treatment area is obtained than would be available with a conventional ointment.

As will be appreciated by a person skilled in the art in view of the above descriptions, in one aspect of the present disclosure, there is provided a method that includes (i) identifying an animal skin treatment area having an adverse skin condition; (ii) determining that the treatment area is at risk for at least one of skin maceration, exposure to ultraviolet radiation and infection; and (iii) based at least in part on the determining, applying a composition to the treatment area, the composition having a viscosity of from about 1 to about 1000 centipoise. The applying includes spraying the composition such that the sprayed composition contacts the treatment area.

In another aspect of the present disclosure, there is provided a method that includes (i) providing a treatment system comprising a dispenser and a treatment composition having a viscosity of from about 1 to about 1000 centipoise; wherein the dispenser comprises a container and an atomizing spray delivery mechanism affixed to the container; and wherein the treatment composition is positioned in the container; (ii) identifying an animal skin treatment area exhibiting signs of an adverse skin condition; (iii) in response to the identifying, passing the composition through the atomizing spray delivery mechanism to atomize the composition and to propel the atomized composition toward the skin treatment area; and (iv) leaving said composition on the skin treatment area to form a coating.

In yet another aspect, the present disclosure provides a method for treating animal skin that includes (i) providing a treatment system comprising an atomizing spray dispenser and a treatment composition; wherein the dispenser comprises a container and an atomizing spray delivery mechanism affixed to the container; and wherein the composition is positioned in the container; (ii) selecting a skin treatment area of an animal; (iii) passing the composition through the mechanism to atomize the composition and to propel the atomized composition toward the skin-treatment area; and (iv) leaving said composition on the skin treatment area to form a coating.

In still another aspect, the present disclosure provides a method that includes (i) identifying an animal skin treatment area having an adverse skin condition; and (ii) in response to the identifying, atomizing a composition such that at least a portion of the atomized composition travels to the skin treatment area, wherein the composition has a viscosity of from about 1 to about 1000 centipoise.

Further embodiments of the above methods include the following:

1. The method of any other embodiment wherein the composition comprises from about 1 percent to about 40 percent by weight of a solid particulate material; from about 20 percent to about 99 percent by weight of a fluid base material comprising at least one Material selected from the group consisting of mineral oil, silicone oil, plant-based oil; and up to about 30 percent by weight of water.

2. The method of any other embodiment wherein the solid particulate material comprises particulate zinc oxide.

3. The method of any other embodiment wherein the particulate zinc oxide has an average particle size of from about 0.01 microns to about 10 microns.

4. The method of any other embodiment wherein the composition further comprises from about 5 percent to about 30 percent by weight of at least one skin conditioning agent such as lanolin.

5. The method of any other embodiment wherein the composition further comprises from about 1 percent to about 10 percent by weight of at least one viscosity-increasing material selected from the group consisting of talc, paraffin wax and microcrystalline wax.

6. The method of any other embodiment wherein the spraying includes atomizing the composition with one of an atomizing spray dispenser, an atomizing pump spray dispenser, a piston-style dispenser, and an aerosol dispenser.

7. The method of any other embodiment wherein the composition comprises from about 20 percent to about 30 percent by weight of the solid particulate material, wherein the solid particulate material is zinc oxide; from about 30 percent to about 60 percent by weight of the fluid base material, wherein the fluid base material comprises mineral oil and cyclomethicone; and wherein the composition further comprises: from about 1 percent to about 16 percent by weight of lanolin; from about 1 percent to about 25 percent by weight of petrolatum; and from about 1 percent to about 10 percent by weight of microcrystalline wax.

8. The method of any other embodiment wherein the adverse skin condition is selected from a wound, a scratch, a rash, inflammation, itching, dryness and cracking.

9. The method of any other embodiment wherein the adverse skin condition is selected from an open wound and a wound that produces exudate.

10. The method of any other embodiment wherein the adverse skin condition is selected from a laceration, an abrasion, and a puncture wound.

11. The method of any other embodiment wherein the animal is a mammal.

12. The method of any other embodiment wherein the treatment composition comprises from about 1 percent to about 40 percent by weight of a solid particulate material, from about 20 percent to about 99 percent by weight of a fluid base material selected from the group consisting of mineral oil, silicone oil, plant-based oil and mixtures thereof, and from 0 percent to about 30 percent water by weight.

13. The method of any other embodiment wherein the fluid base material comprises at least one of cyclomethicone and dimethicone.

14. The method of any other embodiment wherein the composition further comprises a skin emollient such as lanolin.

15. The method of any other embodiment wherein the solid material comprises at least one of talc, calamine and kaolin.

16. The method of any other embodiment, further comprising determining that the adverse skin condition is in need of protection from an environmental factor, including weather or sun; and wherein the composition comprises from about 10 percent to about 30 percent by weight of hydrophobized zinc oxide; and from about 20 percent to about 90 percent by weight of a fluid base material selected from the group consisting of mineral oil, silicone oil, plant-based oil and mixtures thereof.

17. The method of any other embodiment wherein the composition comprises at least one of an anti-bacterial and an anti-fungal material.

18. The method of any other embodiment wherein the animal is selected from the group consisting of horse, cow, pig, sheep, chicken, dog, cat, bird, and other small pet.

Compositions described herein are effective in combating bacterial and fungal infections even without an additional antibacterial or antifungal ingredient since they are hygroscopic and allow diffusion of moisture across the coating to help keep the skin area dry. Possible bacteria that can be killed include: *Clostridium difficile*, Vancomycin Resistant *Enterococcus faecalis* (VRE), Methicillin Resistant *Staphylococcus aureus* (MRSA), *Acinetobacter baumanii, Escherichia coli, Aspergillus niger, Escherichia coli, Bacillus atrophaeus, Mycobacterium bovis, Chlamydia trachomatis, Clostridium perfringens, Pseudomonas aeruginosa, Enterococcus hirae, Salmonella typhi, Candida albicans, parapsilasis, Aspergillus fumigaus Trichophyton mentagrophytes*, and combinations thereof.

Various changes and modifications to the described embodiments described herein will be apparent to those skilled in the art, and such changes and modifications can be made without departing from the spirit and scope of the invention and without diminishing its intended advantages. Additionally, while the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for treating a skin treatment area of a non-human animal having fur or hair, comprising:

identifying a skin treatment area of a non-human animal having fur or hair thereon and exhibiting an adverse skin condition that causes the skin treatment area to have a greater risk, relative to a second portion of the non-human animal's skin that is not affected by the adverse skin condition, for at least one of skin maceration, exposure to ultraviolet radiation, self-inflicted injury and infection, wherein the fur or hair is on or part of the skin treatment area; and spraying onto the skin treatment area, without removing the fur or hair, a composition comprising a solid particulate material suspended in a fluid base material comprising a silicone oil to form a hydrophobic moisture barrier on the skin treatment area, the composition having a viscosity of from about 200 to about 700 centipoise, measured at room temperature using a Brookfield viscometer.

2. The method according to claim 1, wherein the solid particulate material comprises particulate zinc oxide.

3. The method according to claim 2, wherein the particulate zinc oxide has an average particle size of from about 0.01 microns to about 10 microns.

4. The method according to claim 1, wherein the composition further comprises from about 5 percent to about 30 percent by weight of at least one skin conditioning agent relative to the weight of the composition.

5. The method according to claim 4 wherein the skin conditioning agent comprises lanolin.

6. The method according to claim 1, wherein the composition further comprises from about 1 percent to about 10 percent by weight of at least one viscosity-increasing material selected from the group consisting of talc, paraffin wax and microcrystalline wax relative to the weight of the composition.

7. The method of claim 1, wherein the spraying includes atomizing the composition with one of an atomizing spray dispenser, an atomizing pump spray dispenser, a piston-style dispenser; and an aerosol dispenser.

8. The method according to claim 1, wherein the composition comprises:

from about 20 percent to about 30 percent by weight of the solid particulate material relative to the weight of the composition; wherein the solid particulate material is zinc oxide, from about 30 percent to about 60 percent by weight of the fluid base material relative to the weight of the composition, wherein the fluid base material comprises mineral oil and cyclomethicone; and wherein the composition further comprises:

from about 1 percent to about 16 percent by weight of lanolin relative to the weight of the composition;

from about 1 percent to about 25 percent by weight of petrolatum relative to the weight of the composition; and from about 1 percent to about 10 percent by weight of microcrystalline wax relative to the weight of the composition.

9. The method according to claim 1, wherein the adverse skin condition is selected from a wound, a scratch, a rash, inflammation, itching, dryness and cracking.

10. The method according to claim 1, wherein the adverse skin condition is selected from an open wound and a wound that produces exudate.

11. The method according to claim 1, wherein the adverse skin condition is selected from a laceration, an abrasion, and a puncture wound.

12. The method according to claim 1, wherein the non-human animal is a mammal.

13. A method for treating a skin treatment area of a non-human animal having fur or hair, comprising:

providing a treatment system comprising a dispenser and a treatment composition having a viscosity of from about 200 to about 700 centipoise, measured at room temperature using a Brookfield viscometer; wherein the dispenser comprises a container and an atomizing spray delivery mechanism affixed to the container; wherein the treatment composition comprises a solid particulate material suspended in a fluid base material comprising a silicone oil, and wherein the treatment composition is positioned in the container;

identifying a skin treatment area of a non-human animal having fur or hair thereon and exhibiting signs of an adverse skin condition, wherein the fur or hair is on or part of the skin treatment area;

in response to the identifying, without removing the fur or hair, passing the composition through the atomizing spray delivery mechanism to atomize the composition and to propel the atomized composition toward the skin treatment area; and leaving said composition on the skin treatment area to form a hydrophobic moisture barrier on the skin treatment area.

14. The method according to claim 13, wherein the solid particulate material comprises particulate zinc oxide.

15. The method according to claim 13, wherein the fluid base material comprises at least one of cyclomethicone and dimethicone.

16. The method according to claim 13, wherein the composition further comprises at least one skin conditioning agent.

17. The method according to claim 16 wherein the skin conditioning agent comprises lanolin.

18. The method according to claim 13, wherein the solid particulate material comprises at least one of talc, calamine and kaolin.

19. A method for treating a skin treatment area of a non-human animal having fur or hair, comprising:

providing a treatment system comprising an atomizing spray dispenser and a treatment composition; wherein the dispenser comprises a container and an atomizing spray delivery mechanism affixed to the container; wherein the treatment composition comprises a solid particulate material suspended in a fluid base material comprising a silicone oil and has a viscosity of from about 200 to about 700 centipoise, measured at room temperature using a Brookfield viscometer, and wherein the composition is positioned in the container;

selecting the skin treatment area of the non-human animal, wherein the fur or hair is on or part of the skin treatment area;

without removing the fur or hair, passing the composition through the mechanism to atomize the composition and to propel the atomized composition toward the skin treatment area; and leaving said composition on the skin treatment area to form a hydrophobic moisture barrier on the skin treatment area.

20. The method of claim 19 wherein the non-human animal is selected from the group consisting of horse, cow, pig, sheep, dog, cat, and other pet.

21. The method of claim 19, further comprising determining that the adverse skin condition is in need of protection from an environmental factor; and wherein the composition comprises from about 10 percent to about 30 percent by weight of hydrophobized zinc oxide relative to the weight of the composition; and from about 20 percent to about 90 percent by weight of the fluid base material relative to the weight of the composition.

22. The method of claim 19, wherein the composition comprises at least one of an anti-bacterial and an anti-fungal material.

23. The method according to claim 1, wherein the composition further comprises at least one additive exhibiting a taste that is configured to be unpleasant to an animal if ingested.

24. The method according to claim 20, wherein the non-human animal is selected from the group consisting of hamster, gerbil, rabbit, guinea pig, ferret, and mouse.

25. The method according to claim 20, wherein the non-human animal is selected from the group consisting of camel, and zebra.

* * * * *